US005318549A

United States Patent [19]

Yang

[11] Patent Number: 5,318,549

[45] Date of Patent: Jun. 7, 1994

[54] DISPOSABLE URINE BAG

[76] Inventor: Chung-Rong Yang, No. 287-1, Liu-An, Liu-An Li, Chia-Li Chen, Tainen Hsien, Taiwan

[21] Appl. No.: 901,794

[22] Filed: Jun. 22, 1992

[51] Int. Cl.$^5$ .......... A61F 5/44

[52] U.S. Cl. .......... 604/349; 4/144.1

[58] Field of Search .......... 383/42, 51, 905, 35, 383/84; 604/349-353, 364; 128/760, 761, 767; 4/144.1-144.4

[56] References Cited

U.S. PATENT DOCUMENTS

| | | | |
|---|---|---|---|
| 3,189,252 | 6/1965 | Miller | 383/57 |
| 3,859,125 | 1/1975 | Miller et al. | 604/364 |
| 4,453,938 | 6/1984 | Brendling | 604/349 |
| 4,515,840 | 5/1985 | Gatward | 385/905 |
| 4,820,291 | 4/1989 | Terauchi et al. | 604/349 |

FOREIGN PATENT DOCUMENTS

| | | | |
|---|---|---|---|
| 0665840 | 7/1964 | Italy | 383/42 |
| 0325102 | 6/1970 | Sweden | 604/349 |
| 8500791 | 2/1985 | World Int. Prop. O. | 383/42 |

*Primary Examiner*—Randall L. Green
*Assistant Examiner*—Rob Clarke
*Attorney, Agent, or Firm*—Ladas & Parry

[57] ABSTRACT

A urine bag includes a bag body made of a urine impermeable paper and an absorbing body made of an absorbent material which can absorb urine. The bag body has an open upper end and a middle folding line along which the paper is folded so as to define a front sheet and a back sheet on both sides of the middle folding line. Two sides of the front sheet are coupled with two sides of the back sheet so as to define an accommodating chamber between the front and back sheets. Each of the front and back sheets has a curved end edge and a curved cover folding line between which a generally olive-shaped cover portion is defined. The olive-shaped cover portions of the front and back sheets can be folded to overlap each other so as to close the open upper end of the bag body.

3 Claims, 10 Drawing Sheets

DISPOSABLE URINE BAG

BACKGROUND OF THE INVENTION

1. Field of the Invention

This invention relates to a urine bag, more particularly to a disposable urine bag which can easily corrode after it is thrown away so as not to cause environmental pollution.

2. Description of the Related Art

The improvement of this invention is directed to the conventional urine bag shown in FIG. 1. As illustrated, the conventional urine bag (1) has a urine impermeable bag body (11) made of a soft plastic, a support (12) made of a hard plastic, and an absorbing body (13) made of an absorbent material which can absorb urine. The bag body (11) has an accommodating chamber (111) and an open upper end (112) hot sealed on the support (12). The support (12) has a central hole (121) formed therethrough and is communicated with the accommodating chamber (111). The absorbing body (13) is received in the accommodating chamber (111) of the bag body (11).

Referring to FIG. 2, in use, the support (12) is brought into contact with the user so that urine can flow into the accommodating chamber (111) through the central hole (121) of the support (12). The absorbing body (13) absorbs the urine in the accommodating chamber (111).

The urine bag (1) suffers from the following drawbacks:

(1) Because the urine bag (1) is inexpensive, it is normally thrown away after use. However, it is difficult for the plastic urine bag (1) to corrode, causing inevitable environmental pollution.

(2) After use, if the urine bag (1) is not put in an upright position, the urine flows from the bag body (11). This situation requires improvement from a hygienic standpoint.

SUMMARY OF THE INVENTION

An object of this invention is to provide a urine bag made of a paper which can easily corrode so as not to cause environmental pollution.

Another object of this invention is to provide a urine bag with a built-in cover means whereby the urine cannot flow from the urine bag after use.

According to this invention, a urine bag includes a bag body made of a urine impermeable paper and an absorbing body made of an absorbent material which can absorb urine. The bag body has an open upper end and a middle folding line along which the paper is folded so as to define a front sheet and a back sheet on both sides of the middle folding line. Two sides of the front sheet are coupled with two sides of the back sheet so as to define an accommodating chamber between the front and back sheets. Each of the front and back sheets has a curved end edge and a curved cover folding line between which a generally olive-shaped cover portion is defined. The olive-shaped cover portions of the front and back sheets can be folded to overlap each other so as to close the open upper end of the bag body.

BRIEF DESCRIPTION OF THE DRAWING

Other features and advantages of this invention will become apparent in the following detailed description of the preferred embodiments of this invention, with reference to the accompanying drawings, of which.

DETAILED DESCRIPTION OF THE PREFERRED EMBODIMENTS

Figure 1:
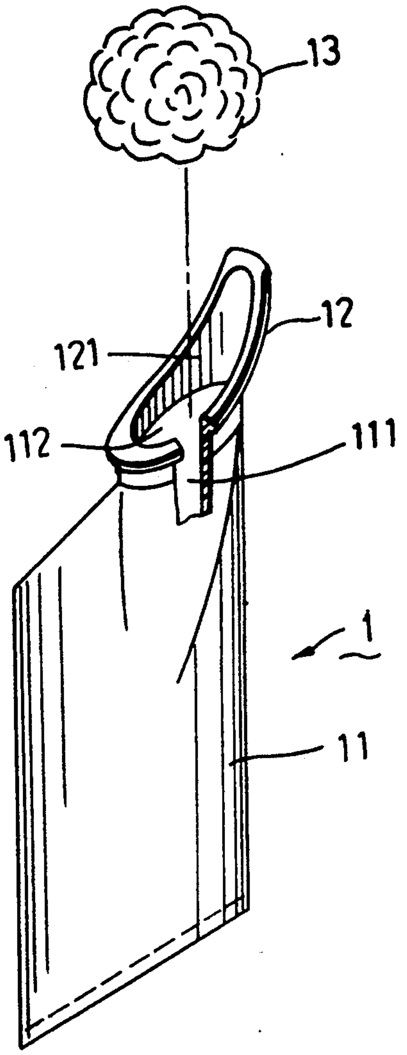
FIG. 1 (PRIOR ART)
FIG. 1 is a perspective view of a conventional urine bag.
Figure 2:
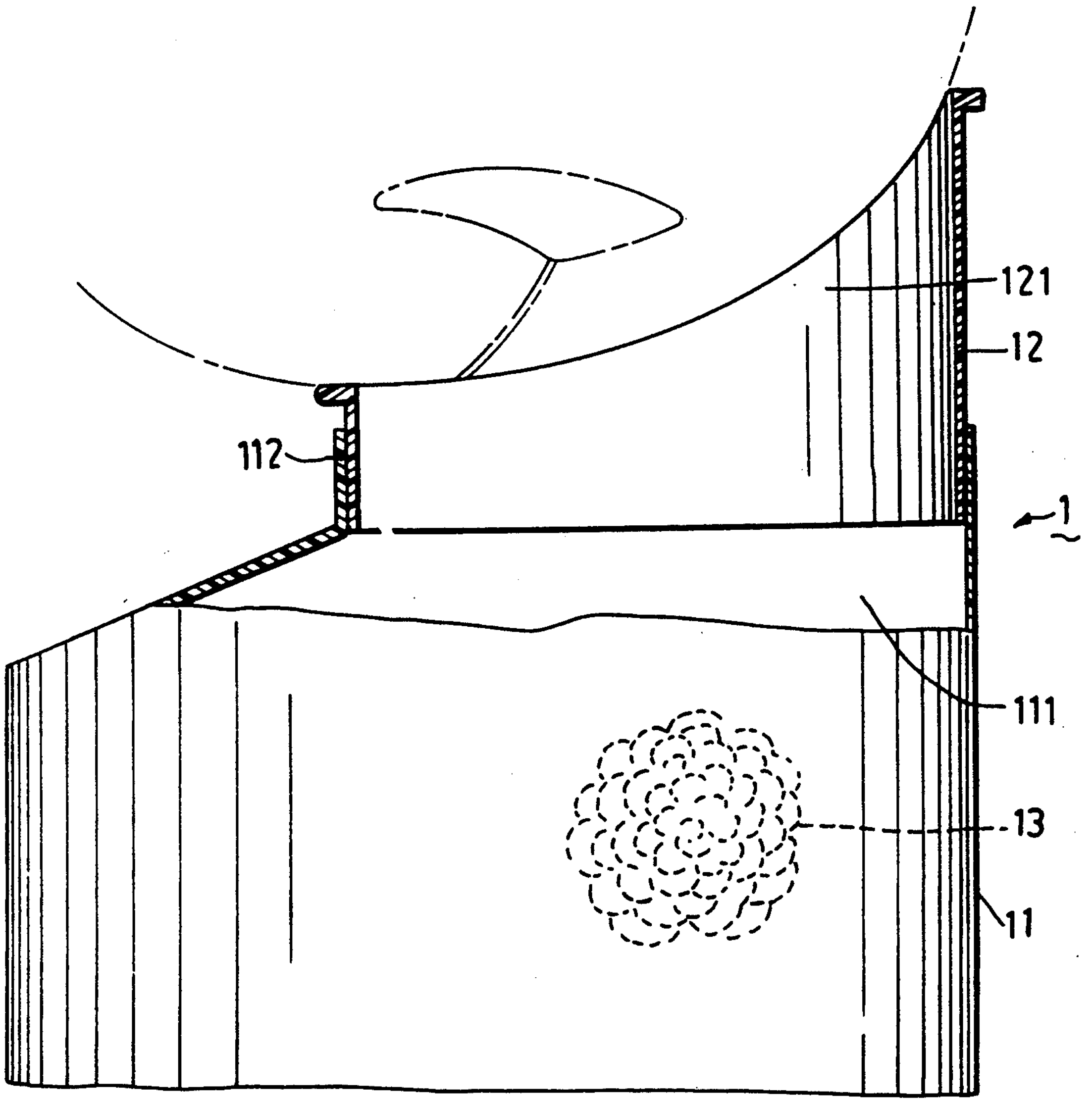
FIG. 2 (PRIOR ART)
FIG. 2 is a schematic view illustrating the use of the conventional urine bag.
Figure 3:
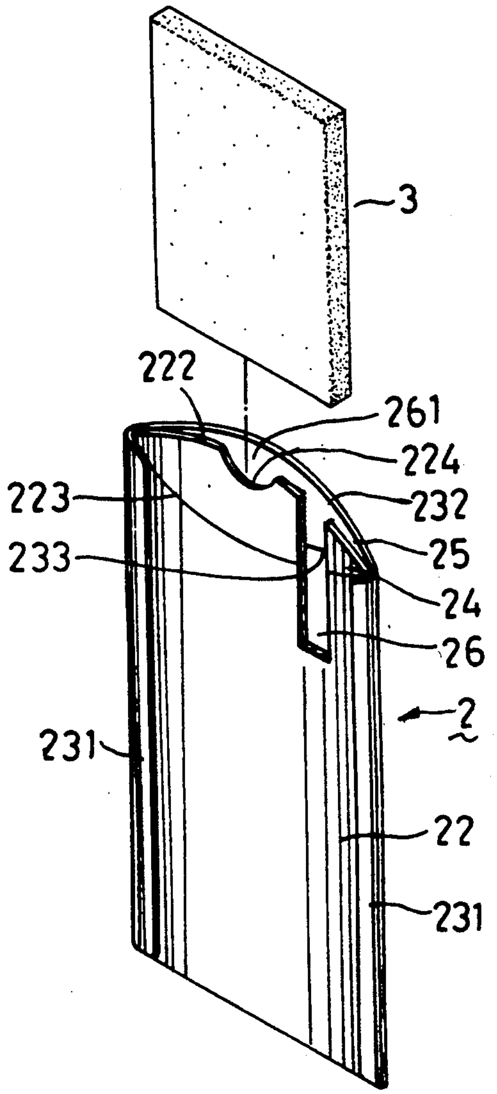
FIG. 3 is a perspective view of a urine bag for male use according to this invention.
Figure 4:
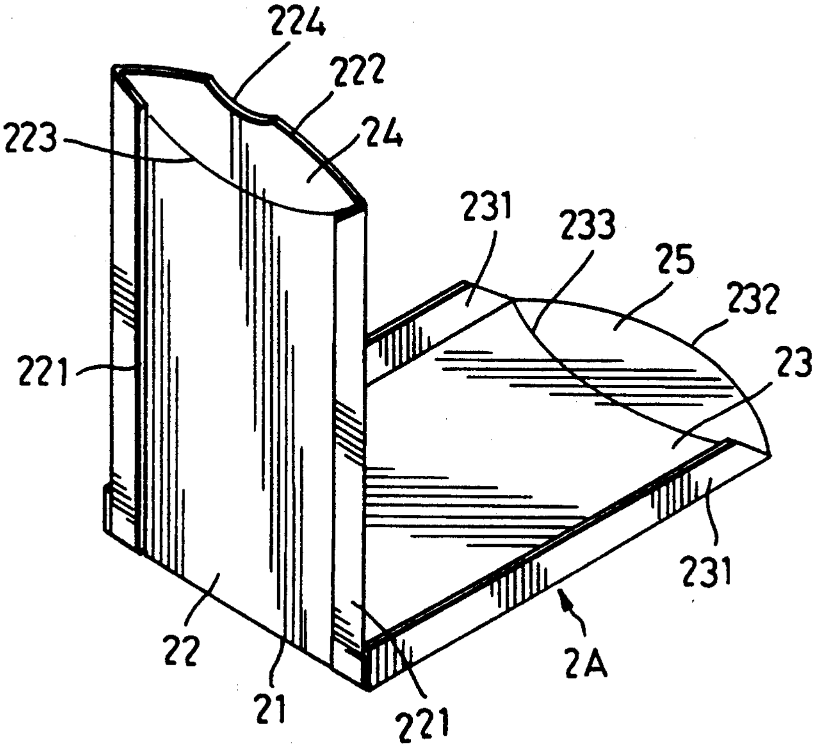
FIG. 4 is a perspective view showing the unfolded bag body of the urine bag for male use according to this invention.

Referring to FIGS. 3 and 4, a urine bag for male use of this invention includes a generally rectangular bag body (2) and an absorbing body (3). The bag body (2) is made of a urine impermeable paper (2A) and has a middle folding line (21) at which the paper (2A) is folded to define a front sheet (22) and a back sheet (23). The front sheet (22) has two elongated foldable wing sheets (221) disposed at two sides thereof, which are folded toward the outward surface of the front sheet (22). Similarly, the back sheet (23) has two elongated foldable wing sheets (231) which are wider than the wing sheets (221) of the front sheet (22).

After the front sheet (22) is folded to contact with the back sheet (23), the wing sheets (231) of the back sheet (23) are folded to cover the wing sheets (221) of the front sheet (22). The folded wing sheets (221, 231) overlap each other so as to minimize flow of urine from the side edges of the bag body (2).

Each of the front and back sheets (22, 23) has a curved end edge (222, 232) and a cover folding line (223, 233) between which an olive-shaped cover portion (24, 25) is defined. The front sheet (22) has an upper end notch (224). The absorbing body (3) is placed in an accommodating chamber (26) (see FIG. 3) which is formed between the front and back sheets (22, 23). In FIG. 3, to illustrate clearly the accommodating chamber (26), a portion of the front sheet (22) is cut away. The bag body (2) has an open upper end (261).

As best shown in FIG. 3, when a male user desires to use the urine bag, the absorbing body (3) is put into the accommodating chamber (26) of the bag body (2). Subsequently, the sharp ends of the olive-shaped cover portions (24, 25) are pressed inward so as to enlarge the open upper end (261) of the bag body (2) to form an olive shape for receiving the urine from the human body of the male user.

Figure 5:
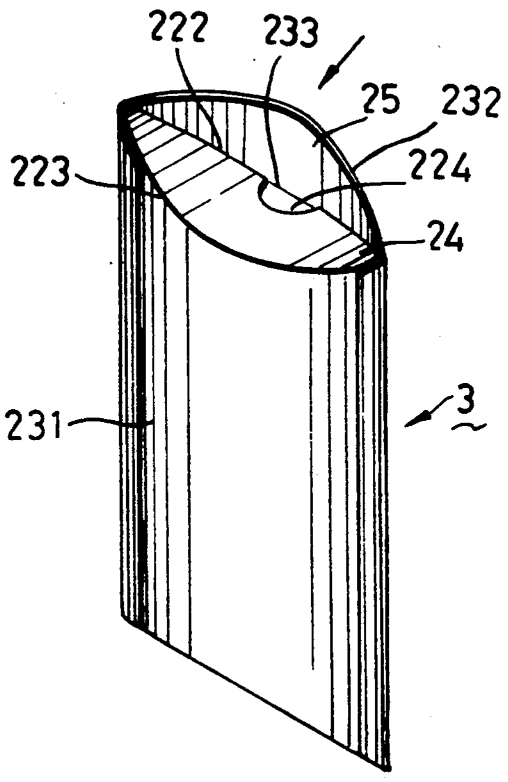
FIG. 5 is a perspective view showing the folded bag body of the urine bag for male use according to this invention.

Referring to FIG. 5, after use, the cover portions (24, 25) of the front and back sheets (22, 23) are folded along cover folding lines (223, 233) to overlap each other so as to close the open upper end (261) of the bag body (2), thereby preventing removal of the absorbing body (3).

Figure 6:
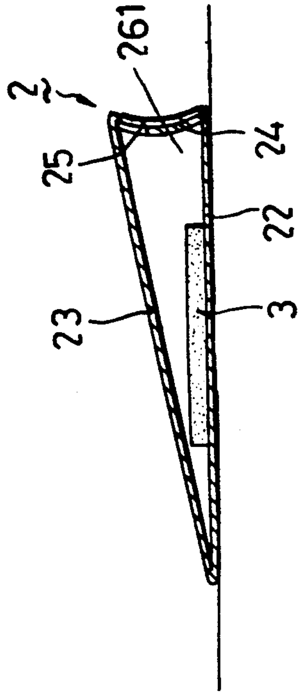
FIG. 6 is a schematic sectional view illustrating the urine bag for male use of this invention, which lies on a horizontal surface.

In FIG. 5, the front cover portion 24 is shown in its folded condition, and the back cover portion 25 is shown not yet folded. With the cover portions (24, 25) positioned horizontally on the open upper end (261), the urine in the bag body (2) cannot escape from the urine bag even when it is placed on a horizontal surface (see FIG. 6).

It is understood that the urine bag shown in FIGS. 3 to 6 is not suitable for female use. To solve this problem, the first embodiment is modified into the form shown in FIGS. 7 to 10. As illustrated, the urine bag for female use according to this invention has a bag body (4) and an absorbing body (5).

Figure 7:
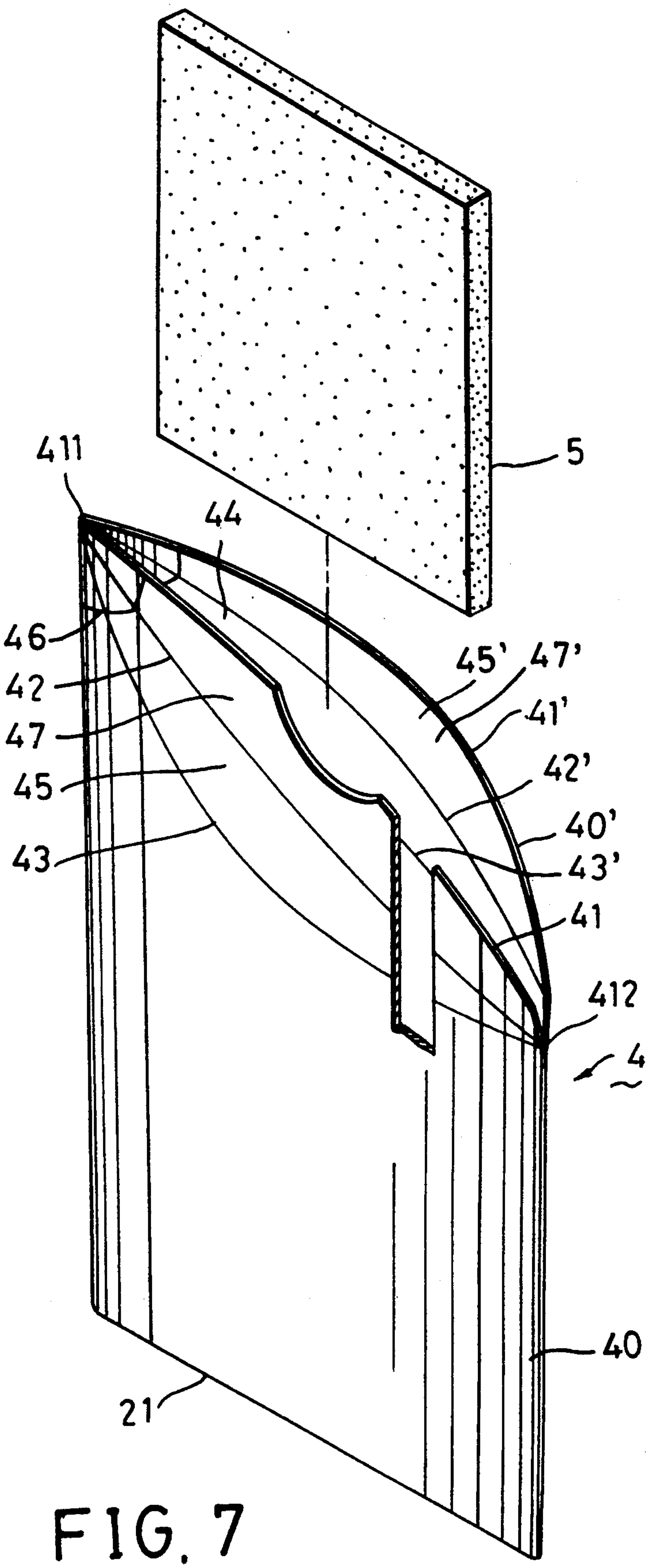
FIG. 7 is a perspective view of a urine bag for female use according to this invention.
Figure 8:
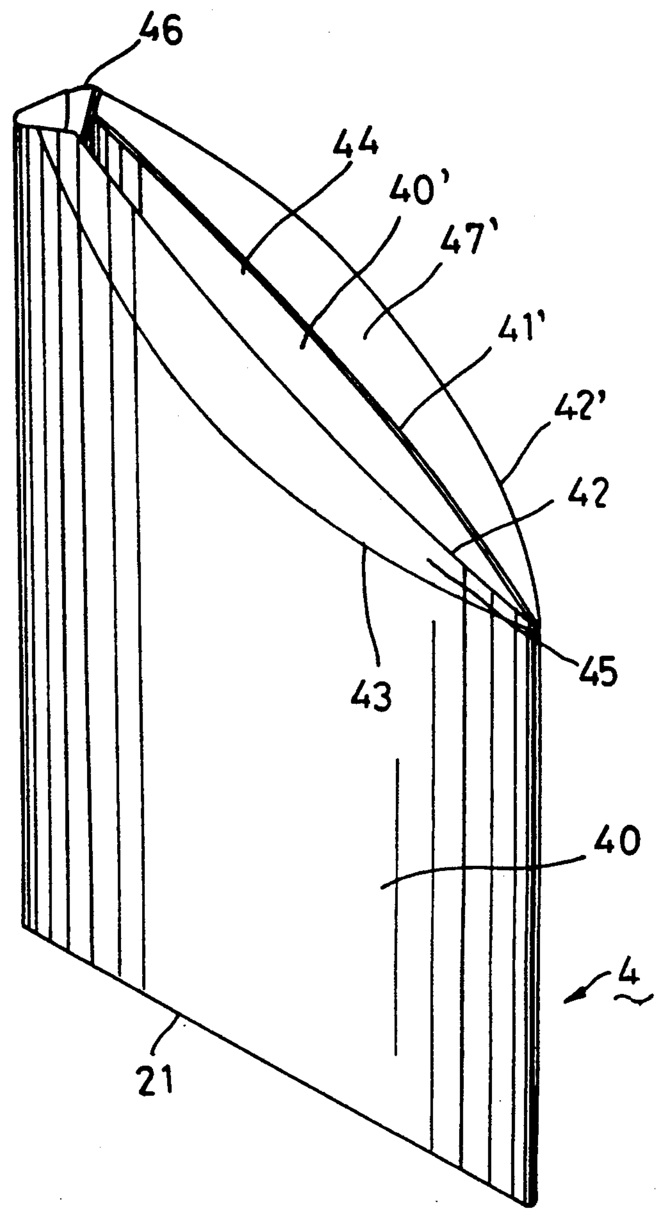
FIG. 8 is a schematic view illustrating how to fold the urine bag for female use when it is in use.

The bag body (4) consists of a front sheet (40) and a back sheet (40'). Each of the front and back sheets (40, 40') has a curved upper end edge (41, 41'), a curved auxiliary folding line (42, 42') positioned under the upper end edge (41, 41'), and a curved cover folding line (43) positioned under the auxiliary folding line (42, 42'). A generally olive-shaped upper end portion (47, 47') is formed between the upper end edge (41, 41') and the auxiliary folding line (42, 42'). In FIG. 7, the curved cover folding line (431) of the back sheet (40') is visible only in a cute away portion of front sheet (40) to illustrate clearly the open upper end (44). An open upper end (44 is formed between the front and back sheets (40, 40'). An olive-shaped cover portion (45, 45') is defined between the upper end edge (41, 41') and the cover folding line (43, 43'). As best shown in FIG. 8, when folded to close the open upper end (44), each of the olive-shaped cover portions (45, 45') is inclined relative to the middle folding line and has a sharp lower end portion (412) and a sharp upper end portion (411) with a curved upper folding line (46).

Referring to FIG. 8, in use, the olive-shaped upper end portions (47, 47') of the front and back sheets (40, 40') are folded downward into the bag body (4) along the auxiliary folding lines (42). Because of the angle of the urine bag depicted in FIG. 8, the front upper end portion (47) is not visible behind front sheet (40). The upper end portions (411) of the cover portions (45, 45') are also folded downward into the bag body (4) along the upper folding line (46). In this situation, the human body can contact comfortably with the cover portions (45, 45'). Furthermore, the urine in the bag body (40) cannot splash from the open upper end (44) due to obstruction of the downward folded upper end portions (47, 47') of the cover portions (45, 45').

Figure 9:
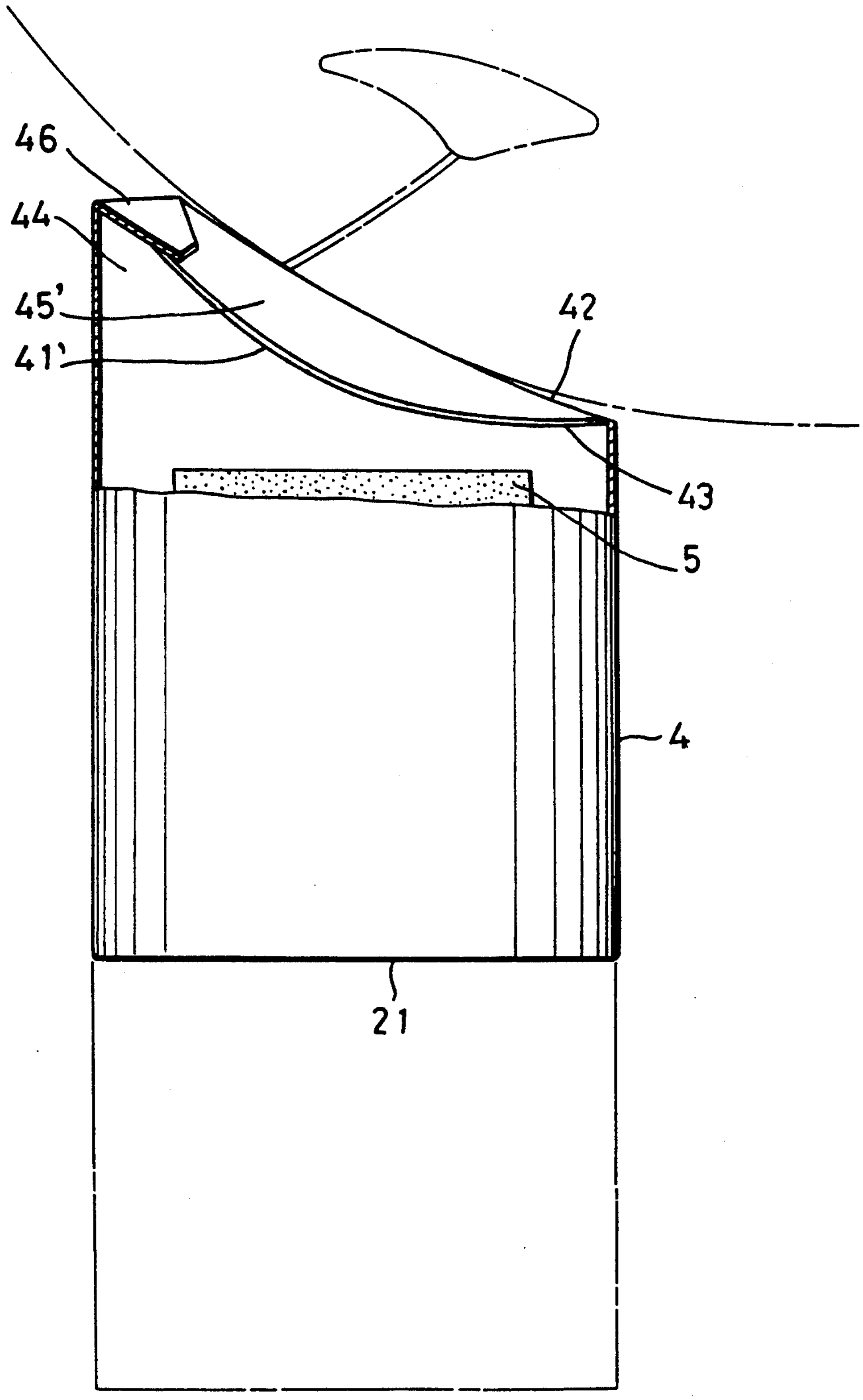
FIG. 9 is a schematic view illustrating the use of the urine bag for female use according to this invention.

FIG. 9 is a partial cross sectional view of the urine bag shown in FIG. 8.

Figure 10:
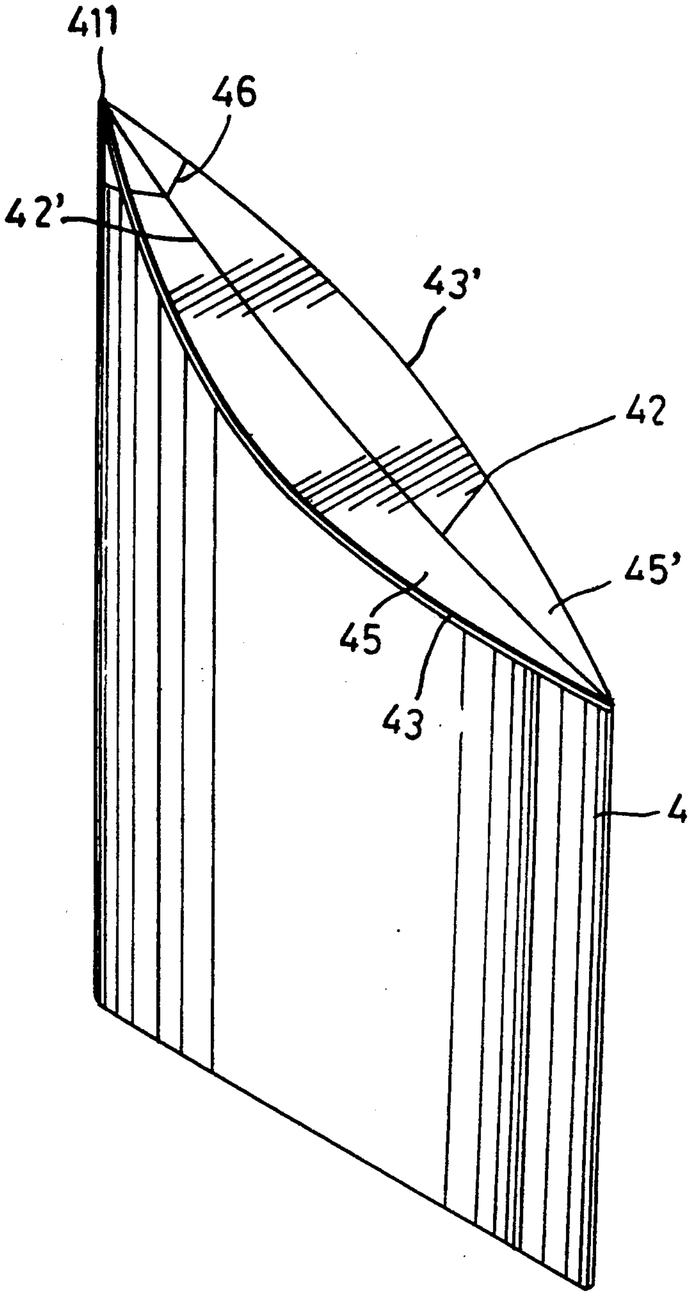
FIG. 10 is a schematic view illustrating how to close the open upper end of the bag body of the urine bag for female use in accordance with this invention.

Referring to FIG. 10, after use, the entire cover portions (45, 45') are folded inward along the cover folding lines (43) to overlap each other so as to close the open upper end (44).

The wing sheets are not shown in FIGS. 7 to 10 due to the fact that they are folded toward the outward surface of the back sheet (40').

With this invention thus explained, it is apparent that numerous variations can be made without departing from the scope and spirit of this invention. It is therefore intended that this invention be limited only as indicated in the appended claims.

I claim:

1. A urine bag comprising:

a bag body made of a urine impermeably paper material having a middle folding line along which said paper material is folded so as to define an upper end open between a front sheet and a back sheet on opposite sides of said middle folding line, two sides of said front sheet being coupled with respective two sides of said back sheet so as to define an accommodating chamber between said front and back sheets, each of said front and back sheets having a curved end edge and a curved cover folding line between which a generally olive-shaped cover portion is defined, said olive-shaped cover portions of said front and back sheets being capable of being folded to over lap each other so as to close said open upper end of said bag body; and an absorbing body made of an absorbent material which can absorb urine, said absorbing body being placed in said accommodating chamber and wherein:

said olive-shaped cover portions of said front and back sheets are inclined relative to said middle folding line after they are folded to close said open upper end of said bag body, each of said olive-shaped cover portions of said front and back sheets having a sharp upper end portion and a sharp lower end portion, whereby said urine bag is suitable for a woman or girl; and each of said olive-shaped cover portions has a curved auxiliary folding line which extends from one end of said olive-shaped cover portion to the other end of said olive-shaped cover portion between said end edge and said cover folding line so as to define a generally olive-shaped upper end portion between said end edge and said auxiliary folding line, whereby when said urine bag is in use, said olive-shaped upper end portions of said front and back sheets are folded downward into said bag body so as to provide a comfortable contact of a user with said bag body along said auxiliary folding lines.

2. The urine bag as claimed in claim 1, wherein said olive-shaped cover portions of said front and back sheet are aligned with and parallel to each other after they are folded to overlap and close said open upper end of said bag body.

3. A urine bag as claimed in claim 1, wherein each of said sharp upper end portions of said olive-shaped cover portions has an upper folding line along which said front and back sheets are folded downward into said bag body so as to provide a comfortable contact of the user with said bag body along said upper folding lines.

* * * * *